United States Patent
Loo (10) Patent No.: US 6,418,966 B2
(45) Date of Patent: Jul. 16, 2002

(54) STOPCOCK FOR INTRAVENOUS INJECTIONS AND INFUSION AND DIRECTION OF FLOW OF FLUIDS AND GASSES

(76) Inventor: George Loo, 9814 Curwood Pl., Beverly Hills, CA (US) 90210

(*) Notice: Subject to any disclaimer, the term of this patent is extended or adjusted under 35 U.S.C. 154(b) by 0 days.

(21) Appl. No.: 09/735,711

(22) Filed: Dec. 12, 2000

Related U.S. Application Data (63) Continuation of application No. 09/004,437, filed on Jan. 8, 1997, now Pat. No. 6,158,467.

(51) Int. Cl.[7] ................................ F16K 11/08
(52) U.S. Cl. ................................ 137/625.47
(58) Field of Search ................ 137/625.41, 625.47

(56) References Cited

U.S. PATENT DOCUMENTS

| | | | |
|---|---|---|---|
| 1,854,307 A | 4/1932 | Hapgood | |
| 2,854,027 A | 9/1958 | Kaiser et al. | 137/625.41 |
| 2,907,349 A | 10/1959 | White | 137/624 |
| 3,405,601 A | 10/1968 | Clarke | 91/4 |
| 4,397,335 A | 8/1983 | Doblar et al. | 137/625.19 |
| 4,669,503 A | * 6/1987 | McGarrity et al. | 137/625.41 |
| 5,445,187 A | * 8/1995 | Farquhar | 137/625.32 |

* cited by examiner

Primary Examiner—John Fox
(74) Attorney, Agent, or Firm—Stetina Brunda Garred & Brucker (57) ABSTRACT

A stopcock comprising having a body and a core. The body has a central chamber and a plurality of connectable ports formed therein that are in fluid communication with the central member. The core is rotatable sealed inside the central chamber. The core has a first cavity, an axially connectable port fluidly connected to the first cavity, and a second cavity formed to be fluidly connectable to two of the plurality of connectable ports in the body, when the core is in a first position. The first cavity is formed to fluidly connect the axially connectable port to one of the two connectable ports when the core is in a second position.

5 Claims, 8 Drawing Sheets

STOPCOCK FOR INTRAVENOUS INJECTIONS AND INFUSION AND DIRECTION OF FLOW OF FLUIDS AND GASSES

This application is a contiuation of Ser. No. 09/004,437 filed Jan. 8, 1998 now U.S. Pat. No. 6,158,467.

FIELD OF THE INVENTION

The present invention relates to a stopcock for use in intravenous injections and infusions, and more particularly to a stopcock having four fluid flow ports and providing four ways for fluid to flow, including two fluid flow paths capable of flowing simultaneously.

BACKGROUND OF THE INVENTION

A stopcock is a cock or valve for stopping or regulating the flow of a fluid (wherein the term "fluid" as used herein may include liquids and/or gasses). In medicine, a stopcock is most typically used for regulating the flow of intravenous ("IV") fluids or medications into, or out of, a patient as part of an intravenous system. A stopcock can also be used to divert fluids or air into devices, such as for filling skin expanders with fluid or air during skin grafting, for filling breast implants with saline during breast augmentation procedures, for diverting spinal fluid into a manometer to measure spinal fluid pressure during a spinal tap, and for diluting viscous packed red blood cells with saline to make them less viscous for subsequent rapid infusion into the patient during transfusions.

Stopcocks have been in use in the practice of medicine for intravenous injection and infusions for more than 30 years. They provide a quick and sterile way for diverting intravenous fluid flow or medication into a patient by changing the flow path in the IV line system.

In the past six years, stopcocks have been used with increasing frequency as a needle-less intravenous injection port. That is, once the initial IV injection port has been opened using a first needle, subsequent injections and infusions are possible through the same injection port via a stopcock having three ports separated by a shut off valve. Stopcocks provide an inexpensive method of avoiding needle-stick injuries and for a clinician to comply with the FDA mandate "to use needle-less injection techniques whenever possible".

The first stopcocks used in medicine were made out of metal. They were re-sterilized and used on other patients. With the refining of plastic injection molding techniques, inexpensive, disposable plastic stopcocks have become the state of the art. They are disposed of after use on a single patient. The disposable plastic stopcock is cost effective and helps prevent spread of diseases between patients.

Early stopcocks were simply used as "on and off" valves to start or stop intravenous infusions. They contained two ports, an inlet port and an outlet port, which were placed in a straight line. There was a shut off lever in the middle of the two ports, and fluid flowed one way. These first stopcocks were designated as two-port, one-way stopcocks.

Another prior art stopcock has a body with three ports which are arranged in a T-shaped configuration, and a core having a lever and an axial portion. The channels and ports can be selected at the option of the user by rotating the lever to a position determined by the direction of flow desired. There is a "stop" tab on the body part of these stopcocks which prevents the lever of the stopcock from being turned to a position where all three ports are open and flow into one another at one time, i.e., such that the T-shaped path of the body and the T-shaped path of the core are fully aligned. Because fluid can flow three different ways, these stopcocks are designated as three-port, three-way stopcocks.

Figure 1A:
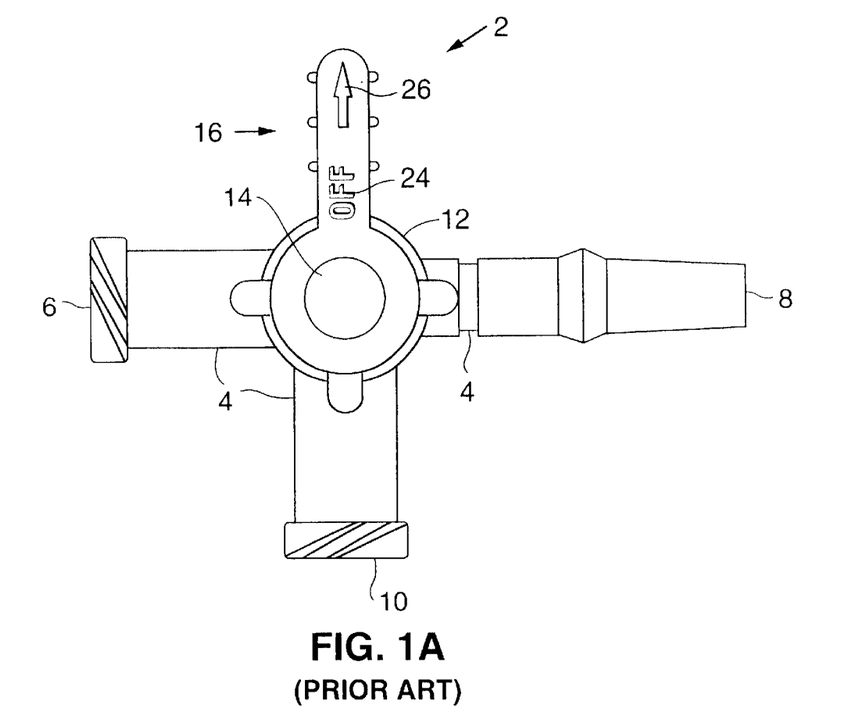
FIG. 1A is a top view of a prior art three-port, four-way stopcock.

Referring to FIG. 1A, the prior art stopcock 2 is a three-port, four-way stopcock. It does not have a stop tab as in the three-port, three-way stopcock to prevent the lever from being turned to a position opposite the right angled port. The stopcock 2 includes a body 4 having an entry port 6, an exit port 8 and an injection port 10, and a core 12. The body 4 and the core 12 are molded as two separate parts and press-fit together to make a completed three-port, four-way stopcock 2. The core 12 includes a rotating axial portion 14 connected to a lever 16.

Figure 1B:
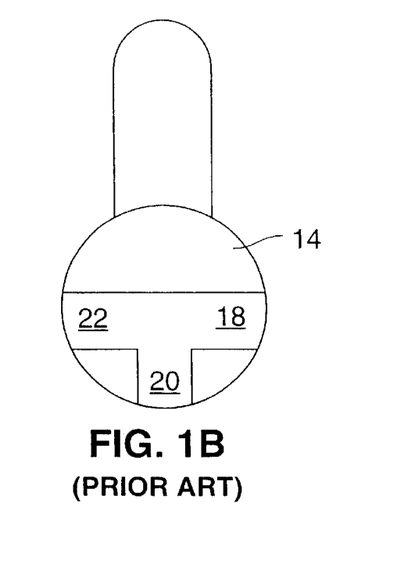
FIG. 1B is a cross-sectional/top view of the T-intersection flow path of a core of a prior art three-port, four-way stopcock.
Figure 1C:
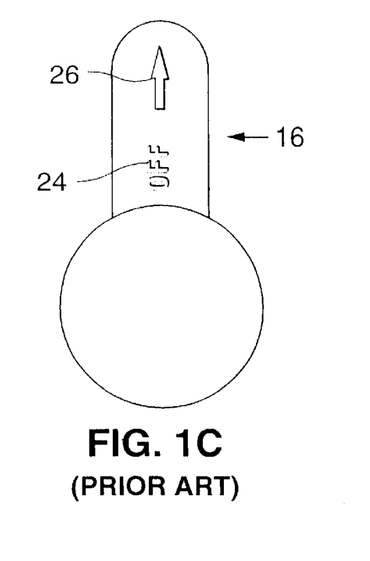
FIG. 1C is a top view of the lever part of a prior art core of a three-port, four-way stopcock.

Referring to FIG. 1B and FIG. 1C, the axial portion 14 of the core 12 has a first flow channel 18, a second flow channel 20 and a third flow channel 22 which form a confluent "T" configuration. The lever 16 generally includes the word "off" 24 and an arrow 26 molded on its upper surface to show which direction fluid will not flow. The arrow 26 and the word "off" 24 do not directly indicate to the user which way the medication or fluid will flow.

The three-port, four-way stopcock 2 is a four-way stopcock because fluid can flow in four different ways. First, when the lever 16 points toward the entry port 6, fluid can flow between the injection port 10 and exit port 8. Second, when the lever 16 points toward the injection port 10, fluid can flow between the entry port 6 and exit port 8. Third, when the lever 16 points toward the exit port 8, fluid can flow between the entry port 6 and injection port 10. Finally, when the lever 16 points opposite the injection port 10, i.e., toward no port, fluid can flow between all three ports 6, 8, 10 at one time.

Figure 2:
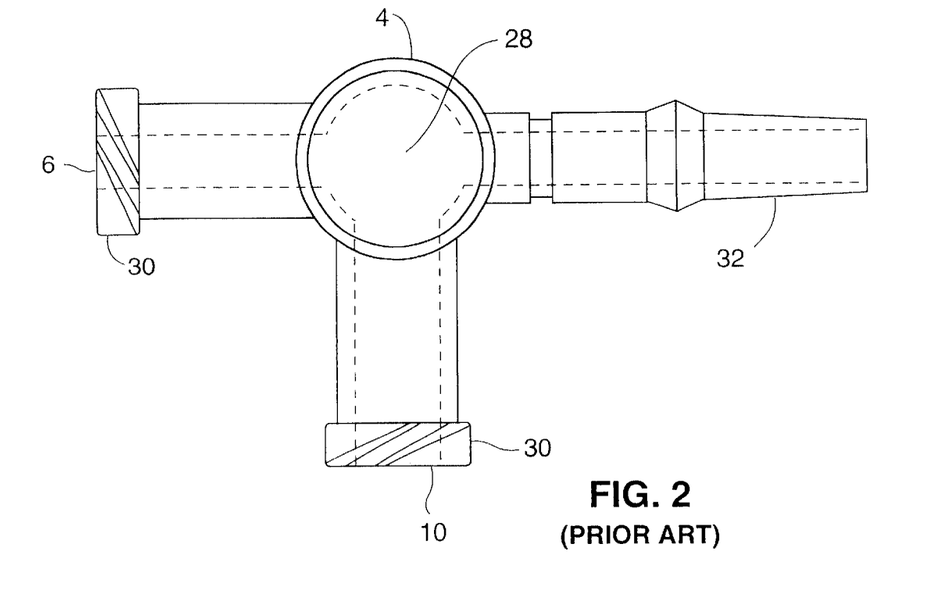
FIG. 2 is a top view of a body of a prior art three-port, four-way stopcock.

Referring to FIG. 2, the body 4 of the three-port, four-way stopcock 2 is molded as one piece. The entry port 6, exit port 8 and injection port 10 are located in a single horizontal plane and are confluent at a central chamber 28, which is filled with the axial portion 14 of the core 12 when the stopcock 2 is assembled. The entry port 6 has a female luer lock connector 30 and is the main fluid entry end of the stopcock 2. It usually is connected to a male luer-lock connector 32 from an IV set connected to a bag of IV fluid. The exit port 8 has a male luer lock or luer slip connector 32 and is the fluid exit end of the stopcock 2 and is usually connected to a female luer lock connector 30 of an IV extension set which ultimately connects to the IV catheter in the patient. The injection port 10 protruding perpendicularly from the middle of the straight line flow path formed by the entry port 6 and exit port 8 has a female Luer lock connector 30 and is used for adding medication or fluids to the IV system.

Figure 3:
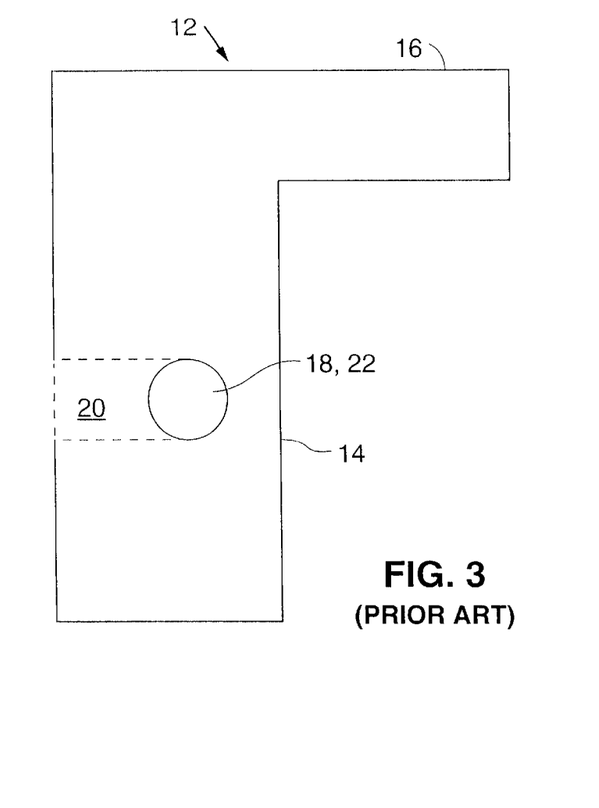
FIG. 3 is a side view of a core of a prior art four-way, three-port stopcock.

Referring to FIG. 3, the axial portion 14 and the lever 16 are molded as one piece in a right angle configuration to form a completed core 12. The lever 16 rotates in a horizontal plane which is parallel to the horizontal plane formed by the three fluid flow ports 6, 8 and 10.

The procedure a clinician must follow to perform a typical IV injection or infusion using a conventional three-port, four-way stopcock 2 is fraught with difficulty and risk. An examination of this procedure makes clear the need for an improvement, such as that of the present invention described further below.

A typical intravenous setup using a three-port, four-way stopcock 2 has the exit port 8 typically connected to an IV extension tubing which is subsequently connected to an IV catheter in the patients vein. The entry port 6 is connected to a main IV administration set which is in turn connected to a bag of IV fluid, and the injection port 10 normally has a syringe or a secondary IV fluid line connected to it. When a syringe is attached to the injection port 10, the bulk and length of the syringe requires that the syringe-stopcock assembly sit on a surface wherein a single plane is formed by the slow ports 6, 8, 10 of the stopcock 2 and the attached syringe. The axial portion 14 then extends vertically upward from, and the lever 16 rotates in a plane parallel to, that surface. To turn the lever 16 in a desired direction, a first hand of a clinician is held palm up in a horizontal plane, with the fingers pointing upward in a vertical direction, to stabilize the syringe-stopcock assembly, and a second hand of the clinician is held above the lever 16, with fingers pointing in a downward, vertical direction, for grasping and rotating the lever 16.

This arrangement is awkward for the clinician. With the first hand below and the second hand above the stopcock 2, the clinician must first determine which way to turn the lever 16 to obtain the desired fluid flow, and then he or she must turn it in the correct direction, either clockwise or counter-clockwise, with fingers of the second hand. When the clinician is assured that the stopcock is secure in the grasp of the first hand only, the second hand releases the lever 16 and grasps the barrel of the syringe attached to the injection port 10. The second hand then pushes or pulls the plunger of the syringe to give an injection of medication or to aspirate fluid. The second hand must next move from the syringe barrel back to its previous position grasping the lever 16 of the stopcock 2 and rotating it back to its original position. This procedure is cumbersome and time consuming, and involves twice moving one hand between two perpendicular planes.

Figure 4:
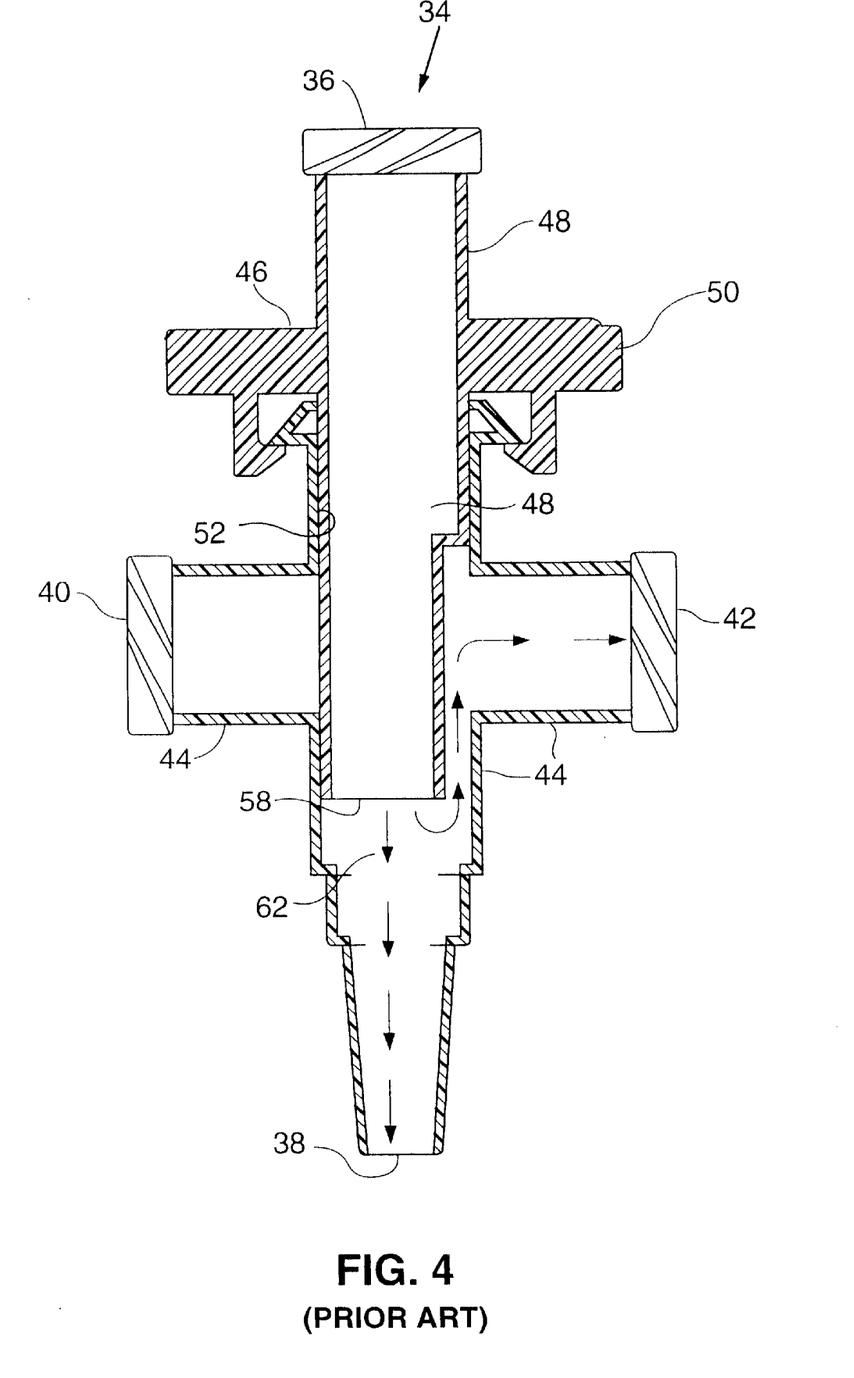
FIG. 4 is a cross-sectional/front view of a prior art four-port, three-way stopcock.

Referring to FIG. 4, there is shown another prior art stopcock. This stopcock is designated a four-port, three-way stopcock 34. Fluid can flow in three different ways. First, the fluid may flow between an entry port 36, an exit port 38, and a first lateral port 40, simultaneously. Second, fluid may flow between the entry port 36, exit port 38 and second lateral port 42 simultaneously. Third, fluid may flow between the entry port 36 and exit port 38 only. The stopcock 34 comprises a body 44 assembled with core 46. The core 46 has an axial portion 48 and a lever 50. The axial portion 48 sits partially inside a central chamber 52 of the body 44 and includes the entry port 36. The body includes the exit port 38, first lateral port 40 and second lateral port 42 which, together with the entry port 36, are confluent to the central chamber 52 such that the body 44 and the core 46 form an air-tight and a fluid-tight connection. The central chamber 52 is only partially filled with the axial portion 48 of the core 46 when the stopcock 34 is fully assembled. The axial portion 48 enters the body 44 through an opening opposite the exit port 38.

Figure 5A:
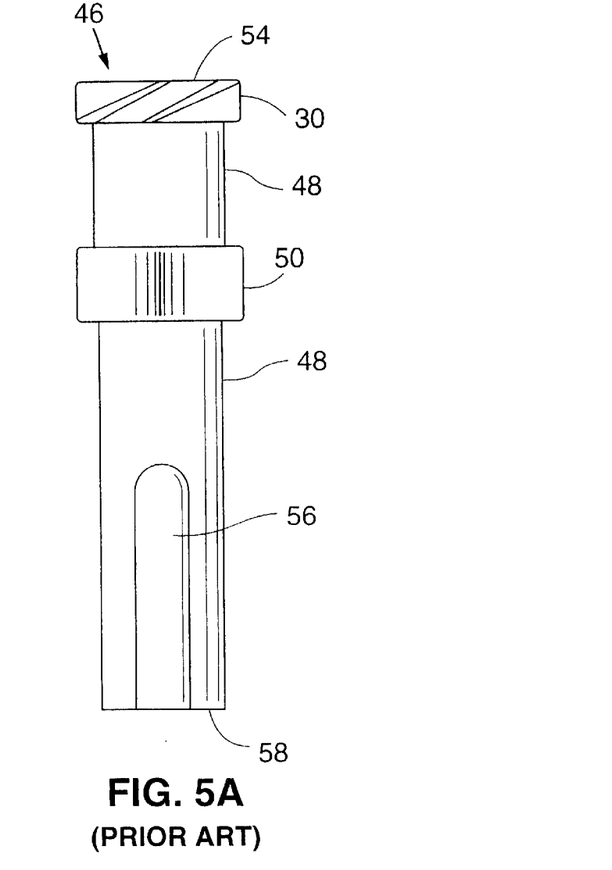
FIG. 5A is side view of a core of a prior art four-port, three-way stopcock.
Figure 5B:
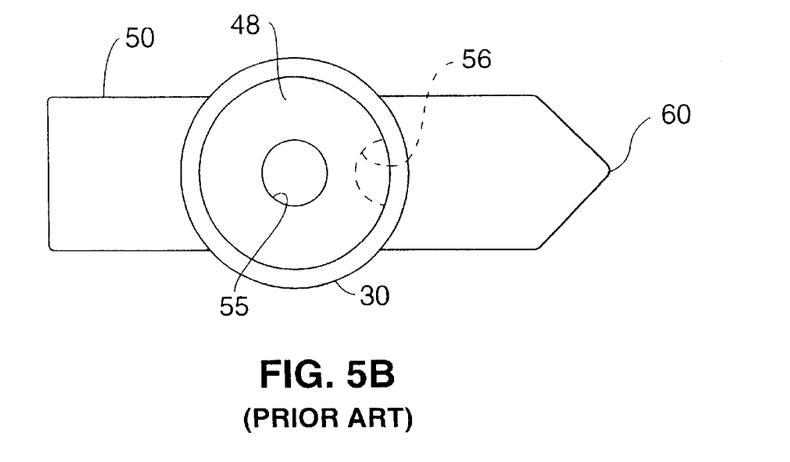
FIG. 5B is a cross-sectional/top view of a prior art core of a four-port, three-way stopcock.

Referring to FIGS. 5A & 5B, the core 46 of the four-port, three-way stopcock is smaller in diameter, and shorter, than the body 44 of the stopcock 34. The lever 50 is built around the axial portion 48 about a third of the way down from its top end 54. The axial portion 48 is vertical and has a hollow cavity 55 at its center extending down its entire length. The axial portion 48 has a female luer connector 30 connected to its top end 54. A groove 56 is carved into the outer surface of the axial portion 48, beginning at its bottom end 58 and going about one third of the way up its length. An arrow-shaped end 60 of the lever 50 points in the direction that the groove 56 faces. The groove 56 is separated from the hollow cavity 55 by a remaining thickness of material comprising the axial portion 48.

Referring back to FIG. 4, the axial portion 48 does not extend to the bottom of the central chamber 52. Thus, there is a small spacing 62 between the bottom of the central chamber 52 and the bottom end 58 of the axial portion, where the groove 56 begins. This spacing and the groove allow fluid to flow between the entry 36, exit 38 and either the first 40 or second 42 lateral ports, simultaneously, if the lever is pointed toward one of the two lateral ports 40, 42. If not, fluid merely flows between the entry 36 and exit 38 ports.

The four-port, three-way stopcock 34 has many drawbacks. First, it lacks the ability to selectively direct IV medications and IV fluids to specific ports and subsequently, to specific parts of the IV system. When the lever 50 is turned toward either of the lateral ports 40, 42, fluid flows between the entry 36, exit 38 and either one of the lateral ports 40, 42, simultaneously, instead of selectively between any two ports. Second, because of the design of the stopcock 34, fluid cannot be directed to flow between the lateral ports 40 and 42. Third, only one continuous flow path can run through the stopcock 34 at one time. Finally, fluid cannot be selectively, and specifically, diverted from either the entry 36 or exit 38 ports to either lateral port 40, 42 because the fluid flow path between the entry 36 and exit 38 ports cannot be shut off, i.e., some fluid will always flow between the entry 36 and exit 38 ports.

SUMMARY OF THE INVENTION

The present invention provides a stopcock having two components, a body and a core, that are assembled together and form a fluid-tight and air-tight seal. The body has a number of connectable ports attached to a central chamber. The core has an axial port and is positioned within the central chamber so that it can be rotated with respect to the body. The core also has two separate, non-communicating fluid passages that can carry fluid between two different sets of ports, simultaneously. For example, the core can be rotated to a position wherein one fluid flows between the axial port of the core and one of the connectable ports of the body, while another fluid simultaneously flow between two other connectable ports of the body.

DETAILED DESCRIPTION OF THE PREFERRED EMBODIMENT

Figure 6:
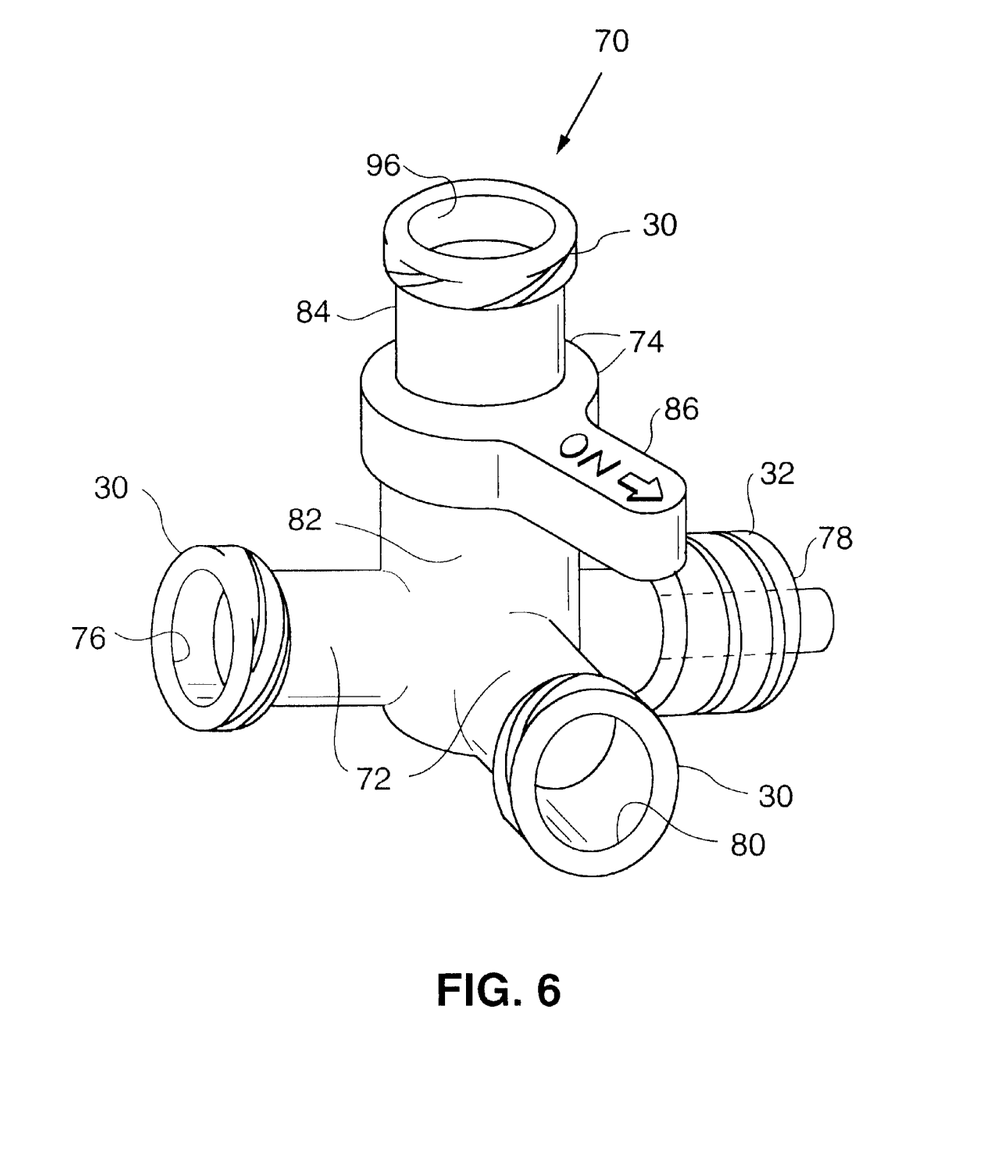
FIG. 6 is a perspective view of a four-port, four-way stopcock of the present invention.

Referring to FIG. 6, a four-port, four-way stopcock 70 of the present invention comprises a body 72 and a core 74. In a preferred embodiment, the body 72 is substantially similar to the body 4 of the three-port, four-way stopcock of FIG. 2. The body 72 includes a main entry port 76, a main exit port 78 and a secondary entry port 80, each being confluent to a central chamber 82. The core 74 has an axial portion 84, an axial port 96 and a lever 86. In a preferred embodiment, the main entry port 76 has a female luer lock connector 30, the main exit port 78 has a male luer lock or luer slip connector 32 and the secondary entry port 80 has a female luer connector 30 attached to its end. In another embodiment (shown in FIG. 9), port 80 may have a male luer lock or luer slip type connector.

Figures 7A, 7B, 7C:
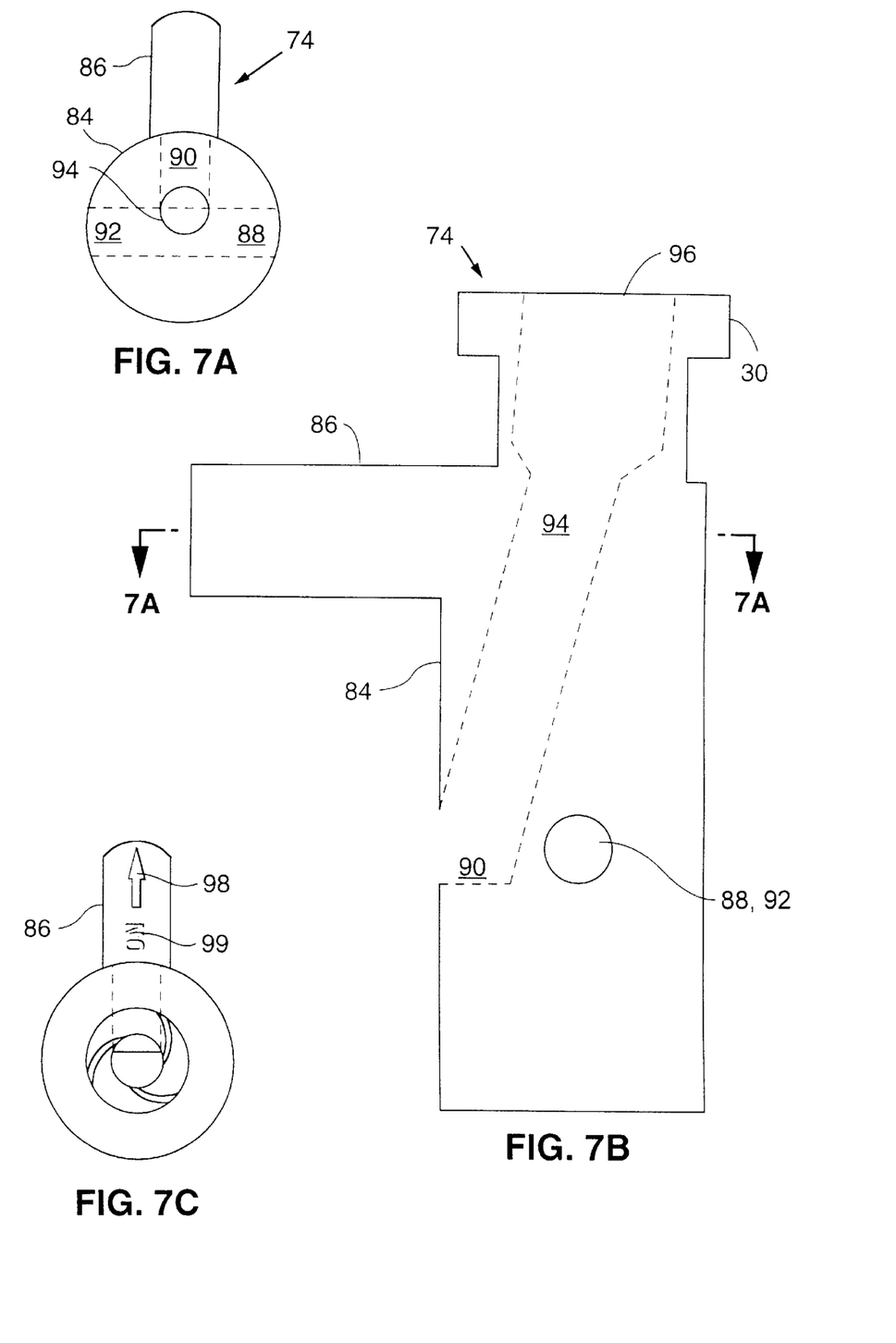
FIG. 7A is a cross-sectional/top view of a core of a four-port, four-way stopcock of the present invention, taken along the line 7A—7A.
FIG. 7B is a side view of a core of a four-port, four-way stopcock of the present invention.
FIG. 7C is a top view of the lever of a core of a four-port, four-way stopcock of the present invention.

Referring to FIGS. 7A and 7B, the axial portion 84 of the core 74 includes a first channel 88, a second channel 90, a third channel 92 and an axial flow channel 94, which ends at the opening of the axial port 96. The first channel 88 and third channel 92 are open to one another, as are the second channel 90 and axial flow channel 94. Neither the first channel 88 nor third channel 92 is open to either the second channel 90 or axial flow channel 94, and vice-versa. The second channel 90 opens in the direction in which the lever 86 points. The openings of channels 88, 90 and 92 are all on the same horizontal plane of the core 74.

Referring to FIG. 7B, the second channel 90 is shorter than the first channel 88 and third channel 92 and does not intersect them. Instead, a remaining thickness of core material separates the fluid flow path defined by the confluent first channel 88 and third channel 92.

The axial portion 84 further includes an axial port 96 which opens vertically above the lever 86. In a preferred embodiment, the axial port 96 includes a female luer-lock connector 30. The axial flow channel 94, which opens at the axial port 96, is not entirely vertical, but is positioned at an acute angle to vertical such that it connects the axial port 96 with the shortened second flow channel 90, yet avoids connection, or communication, with the fluid flow path formed by the first channel 88 and the third channel 92.

The four-port, four-way stopcock 70 of the present invention features two independent fluid flow paths through its core 74. A main fluid flow path is formed by the first channel 88 and third channel 92, and a secondary fluid flow path is formed by the second channel 90 and the axial flow channel 94.

When the core 74 is press-fit assembled to the body 72, the four-port, four-way stopcock of the present invention is complete. The two press-fit parts combine to make an air-tight and a fluid-tight seal.

As the lever 86 is rotated, thereby rotating the core 74, the second flow channel 90 opens in a new direction equal to the direction into which the protruding lever 86 extends. Flow is enabled between the axial port 96 and either the main entry port 76, main exit port 78 or secondary entry port 80 via the axial flow channel 94 when the lever 86 is pointing towards one of these respective ports.

There are four positions of the lever 86 which provide four useful ways for fluid to flow through the stopcock 70. First, when the lever 86 is turned to point in a direction opposite the secondary entry port 80, medication or fluid, such as a syringe or a secondary IV line, attached to the axial port 96 cannot flow because the second flow channel 90 is blocked, as there is norort extending in that direction to accommodate flow. The main fluid flow path is, however, enabled for flow between the main entry port 76 and main exit port 78. Second, when the lever 86 is pointed toward the secondary entry port 80, flow is enabled between the axial port 96 and the secondary entry port 80, as well as between the main entry port 76 and exit port 78, simultaneously. Thus, two independent fluid flow paths through the stopcock 70 are enabled and all four ports are being utilized at the same time. Third, when the lever 86 is pointed toward the main entry port 76, flow is enabled between the axial port 96 and the main entry port 76, no other ports being enabled. Likewise, and finally, when the lever 86 is pointed toward the main exit port 78, flow is only enabled between the axial port 96 and the main exit port 78.

Both aspiration, or flow to the axial port 96, and infusion, or flow from the axial port 96 are possible in conjunction with any of the three horizontal ports 76, 78, 80. A clinician has the additional option of using the secondary entry port 80 for infusion or aspiration with the axial port 96, while at the same time enabling flow between the main entry port 76 and main exit port 78.

Referring to FIG. 7C, the lever 86 has an arrow 98 on its upper surface pointing in a direction in which the lever 86 protrudes. The lever 86 further has the word "ON" 99 written on its upper surface to indicate to the user which way the fluid will flow from or to the axial port 96 into or out of the second flow channel 90. The lever 86 will always point to the specific port that fluid or medication to/from a syringe or secondary IV line attached to the axial port 96 will flow. A clinician can thus immediately know where fluid to or from the axial port 96 will flow.

The improved stopcock of the present invention has the advantage that it has four-ports and can support fluid flow in four different and useful ways. Also, the flow ports are located in two separate planes, three 76, 78, 80 associated with the body 72 in a single horizontal plane and the axial port 96 of the core 74 extending vertically upwards. Prior art devices restrict the possible choices of orientation of the stopcocks and attached medical devices. An additional advantage of the four-port, four-way stopcock 70 of the present invention is that two independent fluid flow paths can be simultaneously enabled. This is not possible with the prior art stopcocks 2 (shown in FIG. 1A), 34 (shown in FIG. 4).

An important clinical situation where the ability to run two separate fluid paths through a stopcock simultaneously would be used, is during blood transfusion. Blood transfusion is a common procedure during surgery and in the post operative care units. Blood is usually obtained from the blood bank in the form of packed red blood cells. The packed red blood cells from the blood bank are cold, and they are a very viscous solution. Packed red blood cells are obtained by separating the fluid plasma from the cells of the whole blood, by centrifuging the blood after the blood has been taken from the donor. The separated blood components are stored in the refrigerator, in the blood bank, to prolong their shelf life. The cold, viscous, packed red blood cells are frequently diluted with saline solution, by the clinician before transfusing them into the patient, to make them less viscous and to warm them up. A warm, and less viscous, solution of red blood cells will flow through an IV system much faster than will a viscous solution of cold packed red blood cells. The ability to transfuse blood rapidly is important when blood must be transfused into a patient as fast as possible to preserve the patient's vital signs.

Figure 8:
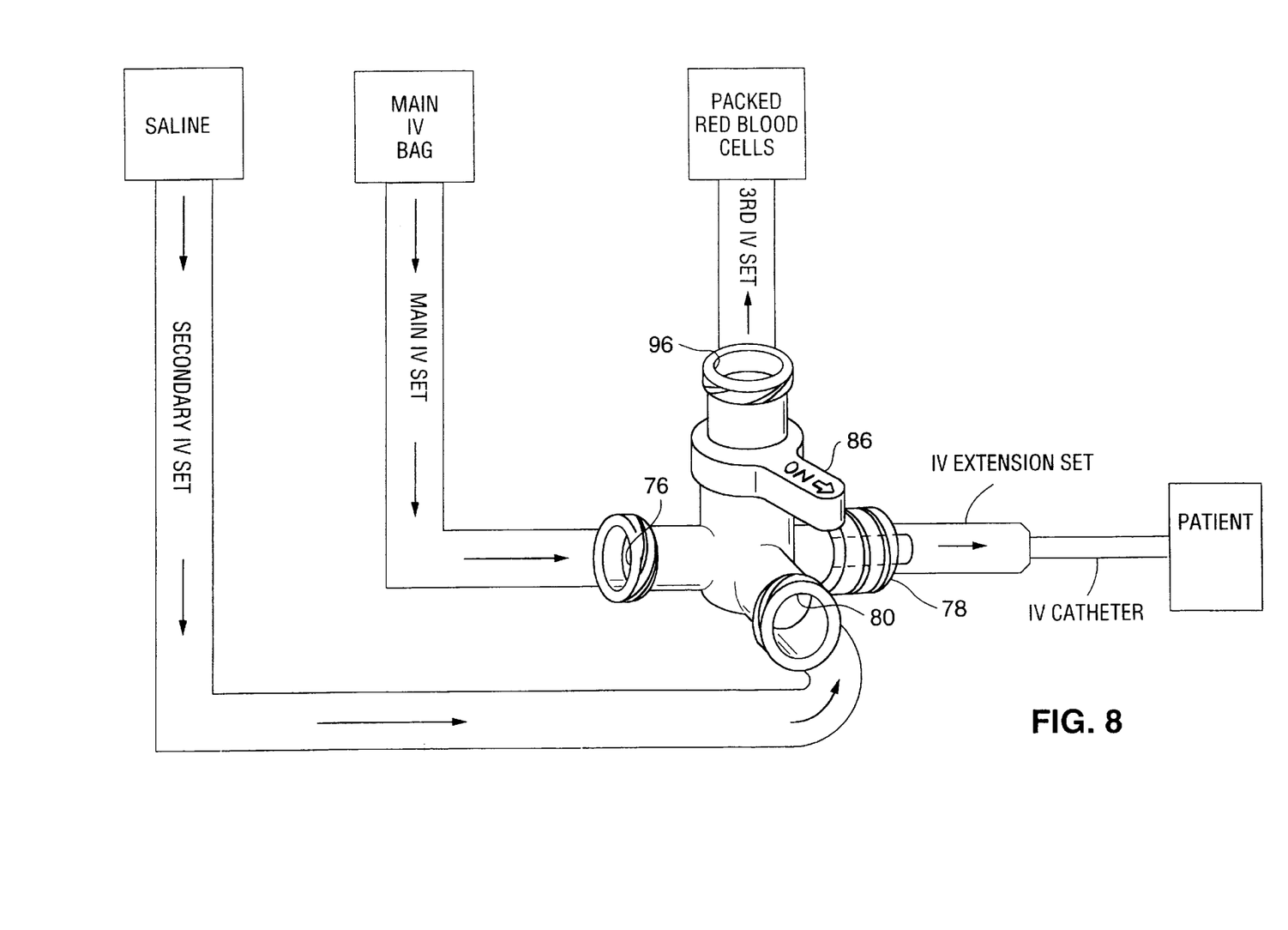
FIG. 8 is a perspective view of a typical IV setup utilizing all four ports and two separate flow paths simultaneously of a four-port, four-way stopcock of the present invention.

Referring to FIG. 8, with the four-port, four-way stopcock 70 of the present invention, the main fluid flow path between the main entry port 76 and main exit port 78 can be used as the main IV line to infuse fluids and medications into a patient, while the secondary fluid flow path between the axial port 96 and secondary entry port 80 can be used to dilute the packed red blood cells. To perform this simultaneous procedure, the lever 86 is first turned to point opposite the secondary entry port 80. This is the "off" position for the axial port 96 because there is no flow port opposite the secondary entry port 80. In this position, medication is now flowing from a main IV set connected to the main entry port 76, through the first channel 88 and the third channel 92, through the main exit port 78, to the IV extension set connected to the IV catheter in the patient.

A bag of saline solution to be used for diluting the packed red blood cells is next attached to a secondary IV set, and a male luer connector 32 of the secondary IV set is attached to the female luer connector 30 of the secondary entry port 80. The bag of packed red blood cells is attached to a third IV set, and the male luer connector 32 of this third IV set is attached to the female luer connector 30 at the axial port 96. After these connections are made, the saline bag is maintained at a level higher than the level of the bag of packed red blood cells.

The lever 86 is next turned to point toward the secondary entry port 80. This enables the diluting saline solution to flow through the secondary IV set attached to the secondary entry port 80, through the second channel 90 and axial flow channel 94, out the axial port 96, through the third IV set and into the bag of packed red blood cells to dilute the viscous packed red blood cells and make them warmer. Turning the lever 86 toward the secondary entry port 80 also permits continued flow through the main IV flow path, and continued therapy to the patient through the main IV line while the packed red blood cells are being diluted through the secondary fluid flow path. Both the main and secondary fluid flow paths of the stopcock 70 of the present invention are thus flowing simultaneously.

When the red blood cells attached to the axial port 96 have been diluted with the saline solution coming from the secondary entry port 80, the lever 86 is next turned to point toward the main exit port 78, and the diluted red blood cells can now flow from the bag of diluted red blood cells, through the third IV set attached to the bag of diluted red blood cells, into the axial port 96, through the axial flow channel 94, out of the main exit port 78 and into the patient.

This technique of red blood cell dilution and subsequent infusion into the patient is done with a simple twist of the lever 86 of the four-port, four-way stopcock 70, and prevents any spillage of valuable blood cells or contamination of any fluids in the IV system. This uninterrupted, red blood cell dilution and transfusion procedure is easily, and sterilely, completed with the four-port, four-way stopcock 70 of the present invention because of the stopcock's ability to enable two separate flow paths at one time.

Figure 9:
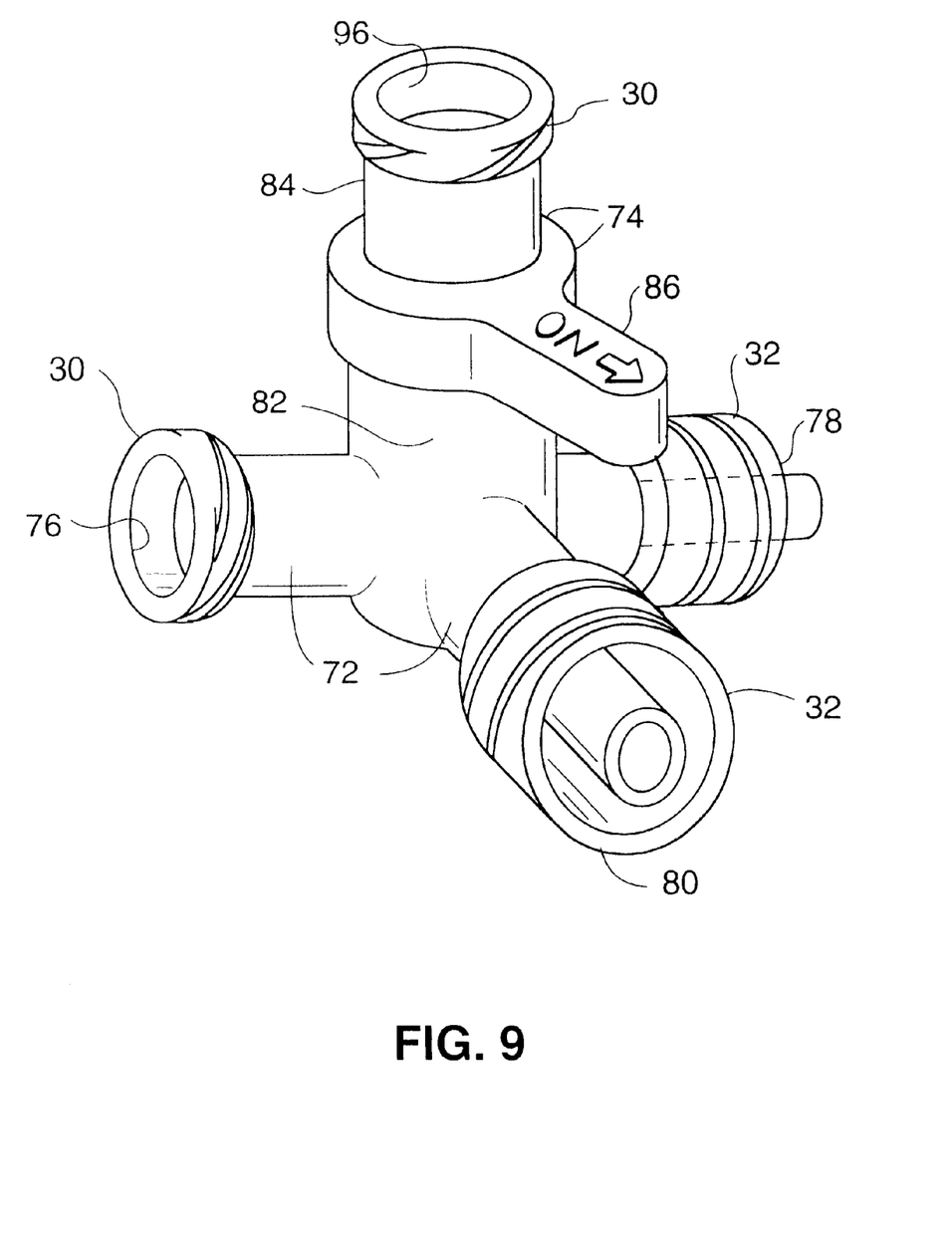
FIG. 9 is a perspective view of another embodiment of a four-port, four-way stopcock of the present invention.

In another embodiment, the secondary entry port 80 would comprise a male luer slip or luer lock fitting. This is an ideal configuration for filling skin expanders or breast implants (which are typically equipped provided with an inflation tube having a female luer connector) with air or fluid from a syringe attached to axial port 96.

CONCLUSION

From the foregoing description, it is believed apparent that the present invention provides a novel four-port, four-way stopcock for intravenous injections and infusions. It should be understood, however, that the invention is not intended to be limited to the specifics of the illustrated embodiments, but rather is defined by the accompanying claims.

What is claimed is:

1. A rotatable core for use with a body to form a stopcock, the body having a central chamber for receiving the core and having entry and exit ports formed therein that are in fluid communication with the central chamber, the core comprising:

a first cavity;

an axially connectable port fluidly connected to the first cavity; and a second cavity formed to be fluidly connectable to the entry and exit ports in the body when the core is in a first position;

wherein the first cavity is formed to fluidly connect the axially connectable port to the exit port when the core is in a second position;

wherein the second cavity is formed to be blocked from fluidly connecting the entry port of the body with the exit port of the body; and wherein the entry and exit ports lie in a plane and the axially connectable port is perpendicular thereto.

2. A rotatable core for use with a body to form a stopcock, the body having a central chamber for receiving the core and having entry and exit ports formed therein that are in fluid communication with the central chamber, the core comprising:

a first cavity;

an axially connectable port fluidly connected to the first cavity; and a second cavity formed to be fluidly connectable to the entry and exit ports in the body when the core is in a first position;

wherein the first cavity is formed to fluidly connect the axially connectable port to the exit port when the core is in a second position; and wherein the entry and exit ports lie in a plane and the axially connectable port is perpendicular thereto.

3. The core of claim 2 wherein the second cavity is formed to be blocked from fluidly connecting the entry port of the body with the exit port of the body.

4. The core of claim 2 wherein the first cavity has a first length making an acute angle with the axially connectable port and a second length making an obtuse angle with the first length.

5. A rotatable core for use with a body to form a stopcock, the body having a central chamber for receiving the core and having entry and exit ports formed therein that are in fluid communication with the central chamber, the core comprising:
- a first cavity;
- an axially connectable port fluidly connected to the first cavity; and
- a second cavity formed to be fluidly connectable to the entry and exit ports in the body when the core is in a first position;
- wherein the first cavity is formed to fluidly connect the axially connectable port to the exit port when the core is in a second position;
- wherein the second cavity is formed to be blocked from fluidly connecting the entry port of the body with the exit port of the body; and
- wherein the first cavity has a first length making an acute angle with the axially connectable port and a second length making an obtuse angle with the first length.

* * * * *